US00PP28190P3

(12) United States Plant Patent
Van Dijk

(10) Patent No.: US PP28,190 P3
(45) Date of Patent: Jul. 11, 2017

(54) ***ANTHURIUM* PLANT NAMED 'ANTHEQIBO'**

(50) Latin Name: ***Anthurium andreanum* L.**
Varietal Denomination: ANTHEQIBO

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 101 days.

(21) Appl. No.: 14/757,018

(22) Filed: Nov. 9, 2015

(65) Prior Publication Data

US 2017/0135272 P1 May 11, 2017

(51) Int. Cl.
*A01H 5/02* (2006.01)

(52) U.S. Cl.
USPC ..... Plt./365

(58) Field of Classification Search
USPC ..... Plt./365
See application file for complete search history.

(56) References Cited

PUBLICATIONS

UPOV hit on anthurium plant named, 'ANTHEQIBO', QZ PBR 44030, published Feb. 15, 2015.*

* cited by examiner

*Primary Examiner* — Anne Grunberg
(74) *Attorney, Agent, or Firm* — Jondle & Associates, P.C.

(57) ABSTRACT

A new and distinct variety of *Anthurium* plant named 'ANTHEQIBO' particularly distinguished by having shiny, bright orange, cordate and very durable spathes that retain the original color for a very long period of time, dark green and long cordate, durable leaves, white spadix with yellow tip, early and rich flowering continuously throughout the year and a plant height of 22 cm to 26 cm, is disclosed.

3 Drawing Sheets

Genus and species: *Anthurium andreanum* L.
Variety denomination: 'ANTHEQIBO'.

BACKGROUND OF THE NEW PLANT

The present invention comprises a new and distinct variety of *Anthurium*, botanically known as *Anthurium andreanum* L., and hereinafter referred to by the variety name 'ANTHEQIBO'. The new variety originated from a hybridization made in March 2008 in Bleiswijk, The Netherlands. The female parent was an orange *Anthurium* pot plant designated '11283-09' (unpatented), and the male parent was a red *Anthurium* plant designated '5432-11' (unpatented).

A single plant was selected in January 2010 and has been asexually reproduced repeatedly by tissue culture in Bleiswijk, The Netherlands over a five-year period. The present invention has been found to retain its distinctive characteristics through successive asexual propagations.

Plant Breeder's Rights for this variety have been applied for in the European Union on Nov. 6, 2014. 'ANTHEQIBO' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, bright orange, cordate spathe;
2) White spadix with yellow tip;

3) Dark green cordate leaves;
4) Easy flowering; and
5) Hardly no pollen production.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 35-week old plant grown in a greenhouse in Bleiswijk, The Netherlands in September 2015.

DESCRIPTION OF THE NEW VARIETY

Figure 1:
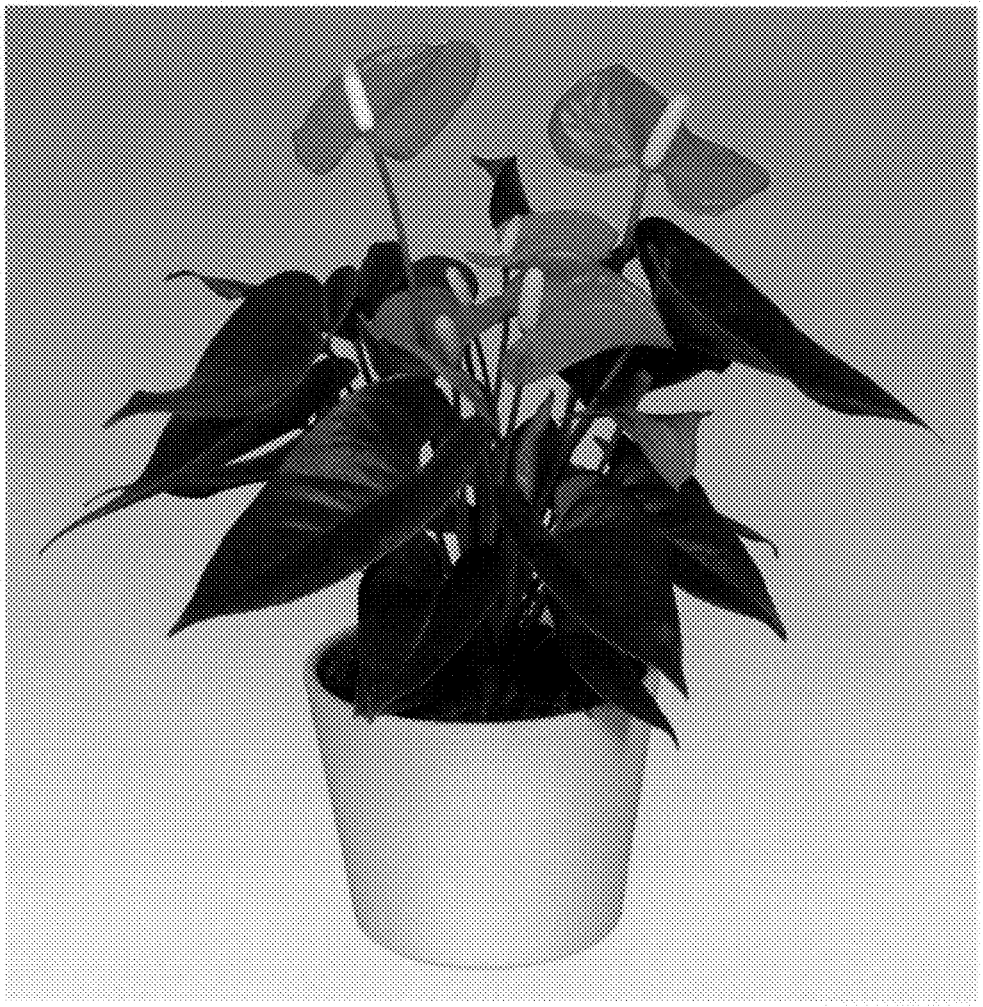
FIG. 1 shows the overall plant habit, including blooms and foliage.
Figure 2:
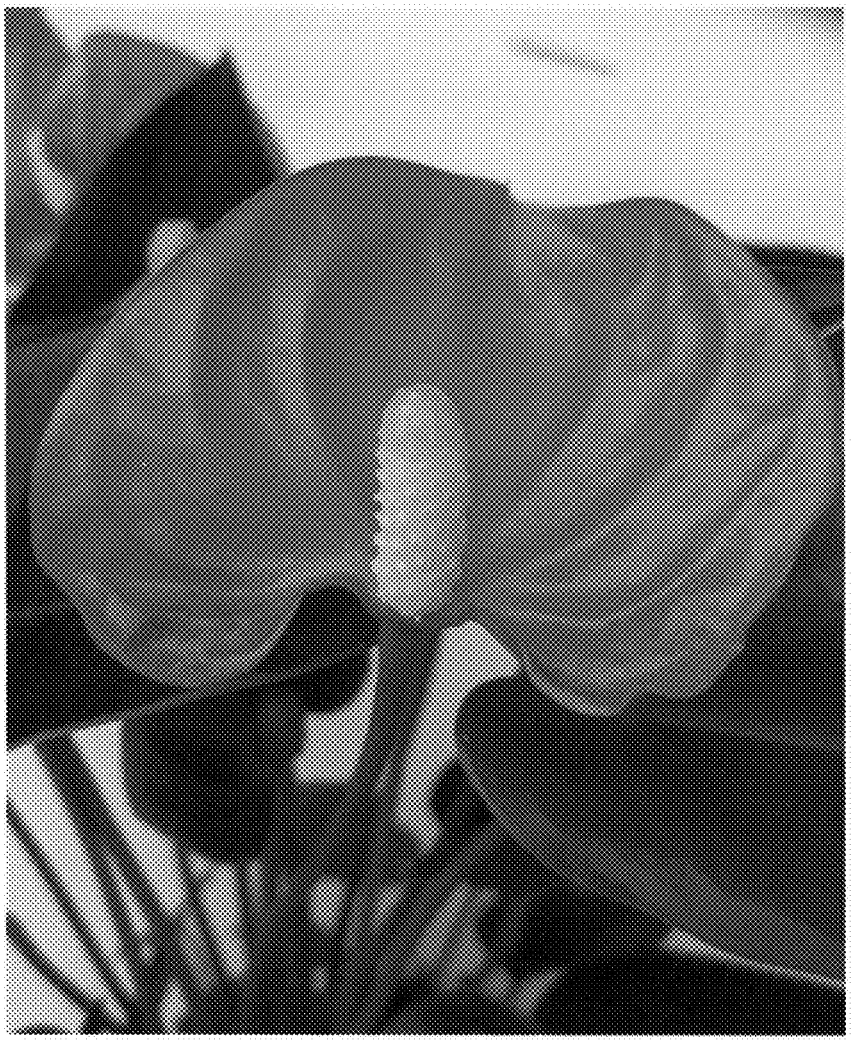
FIG. 2 shows a close-up of the mature spathe.
Figure 3:
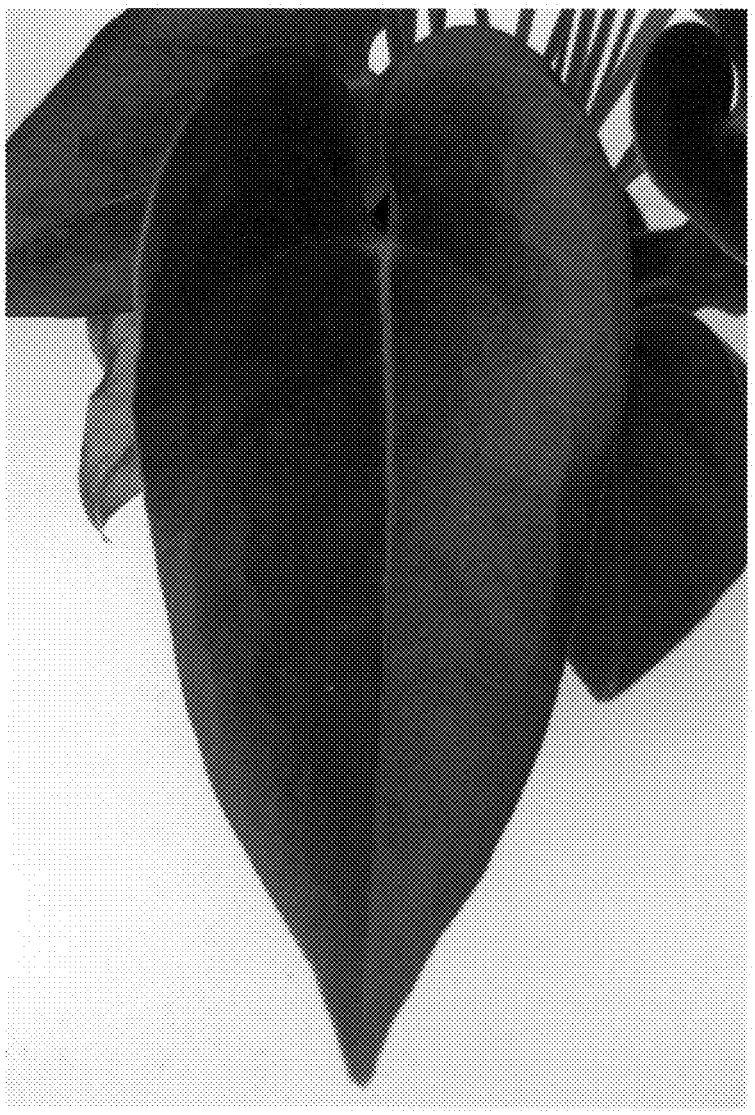
FIG. 3 shows the upper leaf blade surface.

The following detailed description sets forth the distinctive characteristics of 'ANTHEQIBO'. The data which define these characteristics were collected from asexual reproductions carried out in Bleiswijk, The Netherlands. The plant history was taken on 35-week old plants which were planted from tissue culture in 12-centimeter pots and grown in a glass greenhouse between 19° C. and 24° C. Observations were made in September 2015. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family.*—Araceae.

*Botanical.*—*Anthurium andreanum* L.

*Common name.*—*Anthurium.*

*Demonimation.*—'ANTHEQIBO'.

Parentage:

*Female parent.*—*Anthurium* plant '11283-09' (unpatented).

*Male parent.*—*Anthurium* plant '5432-11' (unpatented).

Plant:

*Propagation.*—Tissue culture.

*Root description.*—Fleshy-creamy white colored roots with small hairy lateral roots having yellow-colored root tips.

*Time to produce a finished flowering plant.*—30 to 35 weeks for a 12 cm pot.

*Growth habit.*—Herbaceous perennial.

*Height* (*measured from soil, including inflorescence*).—22.0 cm to 26.0 cm.

*Width* (*measured from leaf tips*).—28.0 cm to 32.0 cm.

Leaves:

*Immature leaves.*—Length: 11.0 cm to 14.0 cm. Width: 5.0 cm to 7.0 cm. Color: Upper surface: RHS 143A. Lower surface: RHS 146B. Texture (both upper and lower surfaces): Shiny.

*Mature leaves.*—Length (fully expanded): 13.0 cm to 16.0 cm. Width: 6.0 cm to 8.0 cm. Shape: Long cordate. Apex: Acute. Base: Cordate. Leaf blade angle with the petiole: Between 100 degrees and 110 degrees. Leaf margin: Entire. Color: Upper surface: RHS 139A. Lower surface: RHS 138A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes.*—Arrangement: Leaf blade has two lobes extending past the petiole. The lobes are non-touching. Length of lobes of mature leaf blades: 1.5 cm to 3.0 cm. Width of lobes of mature leaf blades: 2.5 cm to 3.5 cm. Distance for petiole/leaf junction to highest point on lobes of mature leaf blades: 2.0 cm to 3.0 cm.

*Petiole.*—Cross-section: Round. Diameter: 0.15 cm to 0.25 cm. Length: 12.0 cm to 14.0 cm for a mature leaf size. Color: Mature leaf: RHS 144B. Immature leaf: RHS 144C. Cataphyll color surrounding the petiole: Outside: RHS N144D. Inside: RHS 145D.

*Geniculum.*—Length: 1.0 cm to 2.0 cm. Width: 0.25 cm to 0.35 cm. Color: RHS 144B.

Inflorescence:

*Arrangement.*—Single.

*Flowering habit* (*length of flowering season*).—Continuous.

*Number of inflorescences per plant.*—7 to 9.

*Fragrance.*—Absent.

*Longevity of inflorescence on plant.*—Over a year.

Spathe:

*Buds.*—The spathe is tightly rolled around the spadix and extrudes from the peduncle sheath. After the spathe is fully open the peduncle elongates some extra centimeters.

*Arrangement.*—Spathe angle with the peduncle is between 85 degrees and 90 degrees; the spathe stands on a wiry peduncle about 3.0 cm to 5.0 cm above the foliage.

*Shape.*—Cordate.

*Apex.*—Mucronate.

*Base.*—Cordate.

*Texture.*—Shiny and blistered.

*Margin.*—Entire.

*Size.*—Length: 4.0 cm to 6.0 cm. Width: 5.0 cm to 6.0 cm.

*Lobes.*—Arrangement: The spathe has two lobes extending past the peduncle. The lobes are non-touching. Length: 0.5 cm to 1.0 cm. Width: 1.5 cm to 2.5 cm.

*Color.*—Just fully open: Upper surface: RHS 44B. Lower surface: RHS 41B-C. This orange color remains for a very long period, at least more than 30 weeks after opening.

Peduncle:

*Shape.*—Erect.

*Cross-section.*—Round.

*Length.*—15.0 cm to 18.0 cm.

*Diameter.*—0.2 cm to 0.3 cm.

*Color.*—RHS 144C.

Flowering time:

*General.*—One small rooted untreated tissue culture plant of 8.0 cm tall will flower after 7 to 8 months, depending on the season, and 5 to 7 blossoms appear. More blossoms appear after some additional weeks so that a full flowering and commercial plant will have 7 to 9 orange spathes. Smaller blossoms may occur on less mature plants.

Spadix:

*Size.*—Length: 1.0 cm to 2.5 cm (depending on flower size). Width (at apex): 0.4 cm to 0.5 cm. Width (at base): 0.5 cm to 0.6 cm.

*Shape.*—Columnar.

*Angle from spadix tip to peduncle.*—170 to 180 degrees.

*Texture.*—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color.*—Immature: RHS 17A. Mature: RHS 155B. Aged: RHS N144A.

Flowers:

*Quantity per spadix.*—80 to 100.

*Spadix flower arrangement.*—Bisexual, rounded in cross-section.

*Shape.*—Rounded.

*Size.*—Length: 0.05 cm to 0.1 cm. Diameter (maximum): 0.1 cm.

*Color.*—RHS 155B.

Reproductive organs:

*Stamens.*—Not visible.

*Pollen amount.*—None.

*Pistil.*—Quantity: Many. Length: Less than 0.01 cm. Color: RHS 156D.

*Style.*—Not observed.

*Stigma.*—Shape: Ovoid. Diameter: Less than 0.01 cm. Color: RHS 156D.

*Ovary.*—Rarely visible.

*Ovary color.*—Not measured.

Fruit and seed set: None observed.

COMPARISON WITH PARENTAL AND COMMERCIAL VARIETIES

'ANTHEQIBO' differs from the female parent plant '11283-09' (unpatented) in that 'ANTHEQIBO' has shiny leaves and spathes and produces no pollen, whereas '11283-09' has no shine on its leaves and spathes and produces some pollen.

'ANTHEQIBO' differs from male parent plant '5432-11' (unpatented) in that 'ANTHEQIBO' has orange spathes, whereas '5432-11' has red spathes.

'ANTHEQIBO' differs from commercial variety 'ANTHZUPAP' (U.S. Plant Pat. No. 23,140) in that 'ANTHEQIBO' has a long cordate leaf shape, whereas 'ANTHZUPAP' has a deltoid leaf shape. Additionally, 'ANTHEQIBO' has a smaller spadix length, a smaller spathe width and less shiny spathes than 'ANTHZUPAP'.

'ANTHEQIBO' differs from commercial variety 'ANTHABAZAL' (unpatented) in that 'ANTHEQIBO' has a long cordate leaf shape, whereas 'ANTHABAZAL' has an elliptical cordate leaf shape. Additionally, 'ANTHEQIBO' has a smaller spadix length, a smaller spathe width and a darker orange spathe color than 'ANTHABAZAL'.

I claim:

1. A new and distinct variety of *Anthurium* plant named 'ANTHEQIBO', substantially as illustrated and described herein.

* * * * *